United States Patent [19]

Meier et al.

[11] Patent Number: 5,011,972
[45] Date of Patent: Apr. 30, 1991

[54] BISESTERS OF UNSATURATED CARBOXYLIC ACIDS, THEIR PRODUCTION AND THEIR USE IN CURABLE MIXTURES

[75] Inventors: Helmut-Martin Meier, Ratingen-Eggerscheidt; Harald Pielartzik, Krefeld; Leo Morbitzer, Cologne; Hanns-Peter Müller, Bergisch-Gladbach; Dietrich Braun, Darmstadt-Arheillgen, all of Fed. Rep. of Germany

[73] Assignee: Bayer Aktiengesellschaft, Leverkusen, Fed. Rep. of Germany

[21] Appl. No.: 398,991

[22] Filed: Aug. 28, 1989

[30] Foreign Application Priority Data

Sep. 8, 1988 [DE] Fed. Rep. of Germany ....... 3830453

[51] Int. Cl.$^5$ .............................................. C07C 69/76
[52] U.S. Cl. ..................................................... 560/66
[58] Field of Search .......................................... 560/66

[56] References Cited

U.S. PATENT DOCUMENTS 4,452,993  6/1984  Conciaton et al. .................. 560/66

Primary Examiner—Paul J. Killos
Attorney, Agent, or Firm—Connolly and Hutz

[57] ABSTRACT

The new bisesters of unsaturated carboxylic acids corresponding to the following formula

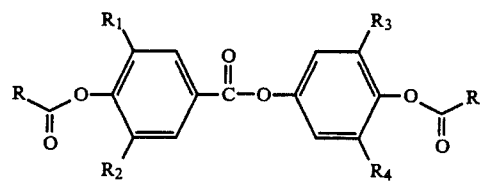

may be used in curable polyester resin mixtures which may in turn be used for the production of moldings. The curable mixtures obtainable from the new bisesters of unsaturated carboxylic acids show a higher glass transition temperature than normal polyester resins and, despite a higher crosslink density, show broader-mesh crosslinking.

4 Claims, No Drawings

BISESTERS OF UNSATURATED CARBOXYLIC ACIDS, THEIR PRODUCTION AND THEIR USE IN CURABLE MIXTURES

This invention relates to new bisesters of unsaturated carboxylic acids, to a process for their production and to their use in curable mixtures.

Unsaturated bisesters, for example bis-acrylates of diphenols, are known as starting products for the production of crosslinked moldings (cf. EP 0 069 069). The use of abrasion-resistant acrylate resins in the dental field is known from JA 79/001 400. The bis-(meth)acrylates described in the Japanese patent publication are described in SU 560 891 as comonomers for the production of illuminants. Other liquid-crystalline acrylates or bis-acrylates and bis-methacrylates are described, for example, by H. Finkelmann in Adv. Polym. Sci. 59/60. Thermosetting anisotropic acrylic polymers of hydroxyethoxy phenol, terephthaloyl chloride and (meth)acryl chloride are described in U.S. Pat. No. 4,683,327. In addition, certain liquid crystalline bis-acrylates are known from Makromol. Chem. 186, 977 (1985) for the production of polymers.

The present invention relates to bisesters of unsaturated carboxylic acids corresponding to formula (I)

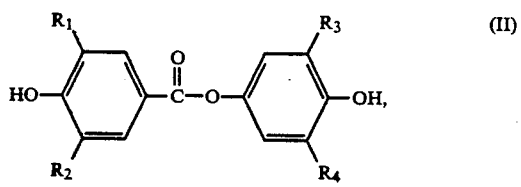

(II)

in which $R_1$, $R_2$, $R_3$ and $R_4$ independently of one another represent hydrogen, halogen or $C_{1-6}$ and preferably $C_{1-4}$ alkyl and R represents residues of unsaturated carboxylic acids. Suitable unsaturated carboxylic acids are acrylic acid, methacrylic acid, 2-butanoic acid, 3-methyl-2-butanoic acid, undecylenic acid, oleic acid, sorbic acid, linoleic acid, preferably acrylic acid, methacrylic acid and 2-butanoic acid.

Fluorine, chlorine and bromine are mentioned as halogens, chlorine being preferred.

Suitable alkyl groups are the methyl, ethyl, propyl, butyl, pentyl and hexyl group and also isomers thereof, preferably methyl, ethyl and propyl.

Particularly preferred compounds of formula (I) are those in which $R^1$, $R^2$, $R^3$ and $R^4$ independently of one another represent hydrogen, chlorine, bromine or $C_{1-4}$ alkyl, such as methyl, ethyl and propyl, and R is derived from acrylic, methacrylic and 2-butanoic acid.

Compounds of formula (I) in which $R^1$, $R^2$, $R^3$ and $R^4$ are hydrogen and R is derived from acrylic acid are especially preferred.

The present invention also relates to a process for the production of the bisesters of unsaturated carboxylic acids corresponding to formula (I)

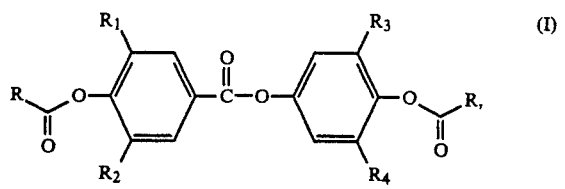

in which $R_1$, $R_2$, $R_3$ and $R_4$ independently of one another represent hydrogen, halogen or $C_{1-6}$ and preferably $C_{1-4}$ alkyl and R represents residues of unsaturated carboxylic acids, characterized in that bisphenols corresponding to formula (II)

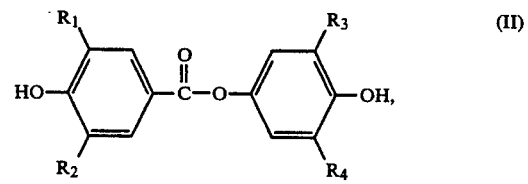

in which $R_1$, $R_2$, $R_3$ and $R_4$ are as defined for formula (I), are reacted with unsaturated acids or reactive derivatives thereof in the presence of catalysts and, optionally, bases.

Suitable unsaturated carboxylic acids are those mentioned above.

The reaction takes place in known manner, as described in Houben-Weyl, Methoden der Organischen Chemie, Carbon-säuren und Carbonsäurederivative (Carboxylic Acids and Carboxylic Acid Derivatives), Supplementary Volume E 5/Part 1, where reactive acid derivatives or activated acids or derivatives thereof are also described.

The bisesters of unsaturated carboxylic acids according to the invention are preferably prepared from the corresponding bisphenol and the corresponding acid halides by a Schotten-Baumann reaction or by the interfacial process.

Tertiary amines, such as tributyl amine and/or triethyl amine, and also ammonium salts, such as triethyl benzyl ammonium or tetrabutyl ammonium chloride and bromide, are preferably used as catalysts during the reaction.

Catalysts for the interfacial reaction are known to the expert and are described, for example, in Compendium of Phase-Transfer Reactions and Related Synthetic Methods, 1979, Fluka AG.

Triethyl amine, diisopropyl amine, pyridine, 2,6-dimethyl pyridine, N,N-dimethyl aniline, 1,8-bis-(dimethylamino)-naphthalene and/or diazabicyclo-(5.4.0)-undec-11-ene may be used as base scavengers in the Schotten-Baumann reaction.

The reaction is preferably carried out in solvents, such as diethyl ether, diisopropyl ether, dioxane, tetrahydrofuran, halogenated hydrocarbons, such as methylene chloride, chloroform, 1,2-dichloroether and/or trichloro-ether.

The production of the bisphenols corresponding to formula (II), in which $R_1$ to $R_4$ are hydrogen, is described for example in EP 252 357.

The present invention also relates to the use of the new bisesters of unsaturated carboxylic acids in curable polyester resin mixtures which may be typically used for the production of moldings.

Accordingly, the present invention also relates to curable polyester resin mixtures containing the bisesters of unsaturated carboxylic acids of formula (I) according to the invention in quantities of from about 5 to 95% by weight and preferably in quantities of from 10 to 50% by weight and unsaturated polyesters in quantities of from 95 to 5% by weight and preferably in quantities of from 90 to 50% by weight.

Unsaturated polyester resins in the context of the invention consist of (A) 30 to 35 and preferably 50 to 90 parts by weight unsaturated polyester and (B) 70 to 5 and preferably 40 to 10 parts by weight monomer copolymerizable with (A).

The unsaturated polyesters suitable for use in accordance with the invention and the monomers copolymerizable with the unsaturated polyesters are known and are described, for example, in J. Björksten et al., "Polyesters and Their Applications", Reinhold Publishing Corp., New York 1956; J. R. Lawrence, Polyester Resins, Reinhold Publ. Corp., New York 1960, pages 18 et seq; Kunststoff-Handbuch, Vol. VIII ("Polyester"), Carl-Hanser-Verlag, München 1973, pages 247–312 and in DE-AS 1 024 654.

The curable mixtures prepared from the bisesters of unsaturated carboxylic acids according to the invention have the following advantages:

They have a higher glass transition temperature than normal polyester resins and, despite a higher crosslink density, show broader-mesh crosslinking. This is surprising because a high crosslink density normally correlates with narrow-mesh crosslinking.

Examples

Example 1

99.6 g (1.1 mol) acrylic acid chloride are added dropwise at room temperature to 115.1 g (0.5 mol) 4-hydroxyphenyl-p-hydroxybenzoate and 111.3 g (1.1 mol) triethyl amine in 500 ml dioxane (approx. 2 hours). The reaction mixture is filtered under suction and washed with cold dioxane. The mother liquor is concentrated in a water jet vacuum, the residue is dissolved in methylene chloride and washed with water until neutral, dried over Na2SO4, filtered and concentrated. The residue is recrystallized from ethanol.

Yield: 100 g yellow-beige solid
Mp.: 99° C.
LC range: 99°–147° C.

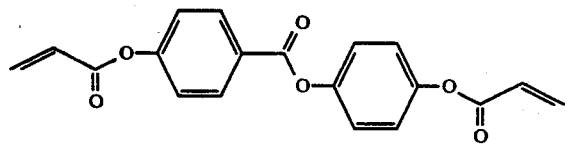

$^1$H—NMR: 8.26–7.27 m, 8H; 6.61, dd, 2H; 6.3, m, 2H; 6.0, dd

Example 2

In a 500 ml three-necked flask equipped with a dropping funnel, internal thermometer and reflux condenser, which has been thoroughly heated in vacuo and purged with nitrogen, 23.01 g (0.1 mol) 4-hydroxybenzoic acid-4'-hydroxyphenyl ester, 20.74 g (0.205 mol) triethylamine and 0.2 g 2,6-di-tert.-butyl-4-methoxy phenol are dissolved in 200 ml anhydrous chloroform. 20.9 g (0.2 mol) freshly distilled methacrylic acid chloride in 20 ml anhydrous chloroform are then added dropwise at such a rate that an internal temperature of 25°–28° C. is established. After stirring overnight at room temperature and washing with distilled water until free from chloride, the organic phase is separated off, dried with Na2SO4 and concentrated. The residue is recrystallized from methanol and dried at room temperature in a water jet vacuum.

Mp.: 149°–151° C.
Yield: 73%
$^1$H—NMR: 8.26 to 7.17, multiplet, 8 arom. protons; 6.39, 6.36, 5.81 and 5.77, 4 vinylic protons; 2.07 and 2.08, singlet, 6 aliphatic protons.

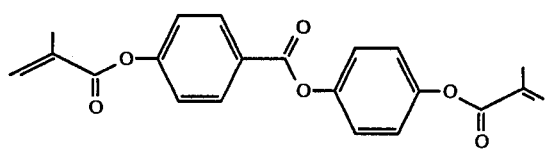

Application Example

An unsaturated polyester resin is prepared from 1514 g 1,2-propylene glycol, 810 g dipropylene glycol, 1919 g maleic anhydride and 588 g phthalic anhydride by melt condensation under nitrogen at 210° C. Dissolved in styrene, this unsaturated polyester resin has the following characteristic data:

Solids content: 80%
Acid value: 20–22 mg KOH/g
Color value: approx. 3
Inhibitor: 0.02% hydroquinone paste
Viscosity: 60,000 mPas 6.4% styrene and 11.3%

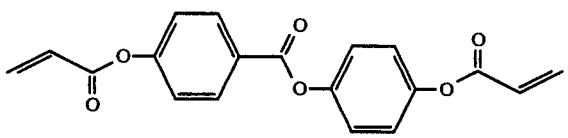

and also 1% benzoyl peroxide are added to this unsaturated polyester resin and the mixture is cured at 80° C. to form a 4 mm thick plate. The plate is conditioned for 65 hours at 80° C. The molding is opaque in appearance and is called F1.

For comparison purposes, a second molding is similarly produced, but without the liquid crystalline component, from the above stock resin by addition of 13.4% styrene. It is called F2. F2 is transparent in appearance.

Modulus measurements produce different results for F1 and F2. F1 shows a narrower, but higher glass transition temperature at 57° C. than F2 which shows a broad, but somewhat lower glass transition temperature. Above the main glass transition temperature (75°–225° C.), the different modulus trends indicate a different crosslink structure. In certain regions, F1 shows broader-mesh crosslinking than F2, which is surprising although the crosslink density of F1 is higher than that of F2.

I claim:

1. Bisesters of unsaturated carboxylic acids corresponding to the following formula

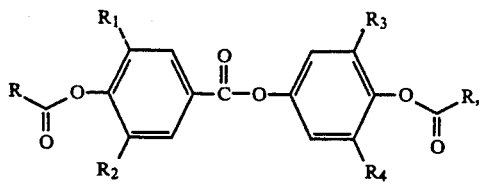

in which

R$_1$, R$_2$, R$_3$ and R$_4$ independently of one another represent hydrogen, halogen or C$_{1-6}$ alkyl and R represents residues of unsaturated aliphatic carboxylic acids.

2. A process for the production of the bisesters corresponding to the formula

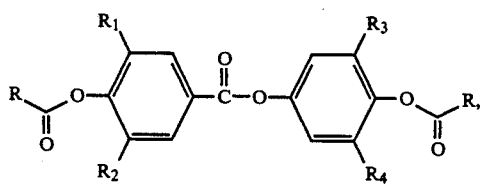

in which

R$_1$, R$_2$, R$_3$ and R$_4$ independently of one another represent hydrogen, halogen or C$_{1-6}$ alkyl and R represents residues of unsaturated aliphatic carboxylic acids, characterized in that bisphenols corresponding to the following formula

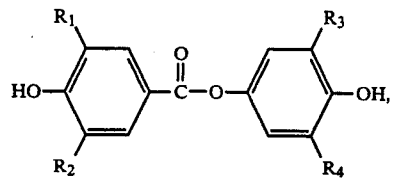

in which

R$_1$ to R$_4$ are as defined above, are reacted with reactive unsaturated aliphatic carboxylic acid derivatives in the presence of catalysts and, optionally, bases.

3. Curable polyester resin mixtures containing 5 to 95% by weight of the bisesters of unsaturated carboxylic acids claimed in claim 1 and 95 to 5% by weight unsaturated polyester resin of which 30 to 95 parts by weight consists of unsaturated polyester and 70 to 5 parts by weight of monomers copolymerizable with the unsaturated polyester.

4. Curable polyester resin mixtures comprising the bisesters according to claim 1.

* * * * *